United States Patent [19]
Semen

[11] Patent Number: 6,056,898
[45] Date of Patent: May 2, 2000

[54] LOW DUST BALANCED HARDNESS ANTIOXIDANT PELLETS AND PROCESS FOR THE PRODUCTION OF SAME

[75] Inventor: John Semen, Baton Rouge, La.

[73] Assignee: Albemarle Corporation, Richmond, Va.

[21] Appl. No.: 09/158,588

[22] Filed: Sep. 22, 1998

[51] Int. Cl.[7] .................................................. C09K 15/28
[52] U.S. Cl. ...................................... 252/400.24; 252/404
[58] Field of Search ............................... 252/400.24, 404

[56] References Cited

U.S. PATENT DOCUMENTS

| | | | |
|---|---|---|---|
| 4,101,512 | 7/1978 | Schmidt et al. | 252/404 |
| 4,692,170 | 9/1987 | Santambrogio | 44/450 |
| 5,597,857 | 1/1997 | Thibaut et al. | 524/400 |
| 5,772,921 | 6/1998 | Gilz et al. | 252/404 |
| 5,846,656 | 12/1998 | Dunski | 252/404 |

*Primary Examiner*—Jacqueline V. Howard
*Attorney, Agent, or Firm*—Philip M. Pippenger

[57] ABSTRACT

The present invention is directed to a process for the production of pellets of a sterically hindered phenol antioxidant such that the pellets have a balanced hardness so as to resist abrasion during conveyance yet being readily dispersed in a host plastic. Such novel pellets are achieved through the use of a processing aid consisting of a solvent selected from the group consisting of methylene chloride, chloroform, toluene, acetone, methylethylketone, xylene, cyclohexane, styrene, methylcyclohexane and hexane having at least 1 gram of antioxidant dissolved therein per 100 grams of solvent and thereafter using the resulting solution of solvent and antioxidant to form a paste of additional portions of the antioxidant which is thereafter extruded, pelleted, and dried. The present invention further provides a novel process for controlling the hardness of a pelleted sterically hindered phenol antioxidant through the addition of from 0 to 80 weight percent of an alcohol of the formula ROH wherein R is an alkyl group of from 1 to 8 carbon atoms to the solvent system employed in the preparation of the processing aid and paste of antioxidant for further processing. The hardness of the resulting pellets is inverse to the amount of alcohol employed in the system.

28 Claims, No Drawings

LOW DUST BALANCED HARDNESS ANTIOXIDANT PELLETS AND PROCESS FOR THE PRODUCTION OF SAME

FIELD OF THE INVENTION

The present invention relates to low dust pellets of a sterically hindered phenol antioxidant having a balanced hardness and to a process for the production of such balanced hardness pellets.

BACKGROUND OF THE INVENTION

Organic polymers (plastics) and in particular polyolefins such as polyethylene and polypropylene require the addition of various additive systems thereto in order both to be processed and to retain long term stability in order to retain desired service properties. In addition to the damaging influence of light and heat, residues of the catalyst system used in the production of such plastics are also detrimental. To overcome such difficulties a wide variety of substances are known in the art for use as additives and stabilizers. In many instances a mixture of such additives is employed.

One commonly used additive system is that comprising a sterically hindered phenol antioxidant which is employed either alone or in combination with an organic phosphite and/or an acid neutralizer. Since such antioxidants are in the powder form, there is presented a disadvantage in the use of same in an additive system due to the problem of dusting as well as having a tendency toward separation and proving difficult to meter. Thus there exists a need for a commercial form of antioxidant additives which does not have these disadvantages.

While a variety of approaches have been made to achieve the production of a low dust additive system, such process have generally employed systems that introduce into the additive package a further component such as calcium stearate, water or other binders. Such a system is that disclosed in U.S. Pat. No. 5,597,857 wherein at least 10 percent by weight of calcium stearate is employed as a binding agent in the formation of additive granules.

Other prior art systems using mixing processes or compacting using a pellet press are known but in most cases the resulting commercial forms do not have adequate mechanical properties.

In addition to an additive package or pellet having adequate mechanical strength or hardness so as to have sufficient abrasion resistance to preclude dust formation, such a pellet needs also to have a balanced hardness which will permit it to be readily processed in the systems wherein the additive package is being dispersed into the host plastic.

Accordingly, there remains a need for a balanced strength antioxidant additive system which possess adequate mechanical strength to avoid mechanical abrasion and dust formation while at the same time having a balanced hardness which will permit it to be readily dispersed in the host plastic while at the same time avoiding the introduction of undesired components.

It is thus an object of the present invention to provide a process for the production of a novel pellet of a sterically hindered phenol antioxidant which will avoid the introduction of undesired components into the additive system.

Another object of this invention is to provide a novel sterically hindered phenol antioxidant system in a pellet form which will have a balanced hardness so as to provide adequate abrasion resistance yet being readily dispersed in a host plastic.

Other aspects, objects and the several advantages of this invention will become apparent from the following specification and claims.

SUMMARY OF THE INVENTION

In accordance with one embodiment of the present invention I have discovered that a pellet of a sterically hindered phenol antioxidant having a balanced hardness so as to provide adequate abrasion resistance while being readily dispersible in a host plastic can be produced by a process which comprises:

(a) dissolving a first portion of said sterically hindered phenol antioxidant in a solvent consisting essentially of at least one solvent of the group consisting of methylene chloride, chloroform, toluene, acetone, methylethylketone, xylene, cyclohexane, styrene, methylcyclohexane and hexane so as to form a solution of said sterically hindered phenol antioxidant in said solvent;

(b) contacting a second portion of said sterically hindered phenol antioxidant with said solution of step (a) in an amount sufficient to form a paste of said second portion of said sterically hindered phenol antioxidant;

(c) extruding the resulting paste of said sterically hindered phenol antioxidant as formed in step (b) so as to form strands thereof;

(d) cutting the resulting strands of said sterically hindered phenol antioxidant as formed in step (c) so as to form pellets thereof, and (e) drying the resulting pellets of said sterically hindered phenol antioxidant as formed in step (d) so as to form dried pellets thereof having a balanced hardness.

In accordance with another embodiment of the present invention, I have discovered that the balance of hardness properties of the pelleted sterically hindered phenol antioxidant can be appropriately modified by the inclusion in the solvent system being employed for the production of the pellets of sterically hindered phenol antioxidant as above described from 0 to 80 weight percent of an alcohol of the formula ROH wherein R is an alkyl group of 1 to 8 carbon atoms.

Thus there is further provided a process for the production of pellets of a sterically hindered phenol antioxidant having a balanced hardness which comprises dissolving a first portion of said sterically hindered phenol antioxidant in a solvent system consisting of at least one solvent of the group consisting of methylene chloride, chloroform, toluene, acetone, methylethylketone, xylene cyclohexane, styrene, methylcyclohexane, and hexane and from 0 to about 80 weight percent of an alcohol of the formula ROH wherein R is an alkyl group of from 1 to 8 carbon atoms, said alcohol being in amounts to said solvent such that as the amount of said alcohol added is increased, there is achieved a decrease in the balanced hardness of the pellet of said sterically hindered phenol antioxidant formed therewith and as the amount of said alcohol is decreased, there is achieved an increase in the balanced hardness of the pellet of said sterically hindered phenol antioxidant formed therewith;

(b) contacting a second portion of said sterically hindered phenol antioxidant with the solution of solvent and alcohol and sterically hindered phenol antioxidant dissolved therein in an amount sufficient to form a paste of said second portion of said sterically hindered phenol antioxidant;

(c) extruding the resulting paste of said sterically hindered phenol antioxidant so as to form strands thereof;

(d) cutting the resulting strands of said sterically hindered phenol so as to form pellets thereof; and (e) drying the resulting pellets of said sterically hindered phenol antioxidant so as to form dried pellets thereof having a balanced hardness which is inverse to the amount of alcohol present in the solvent/alcohol system.

DETAILED DESCRIPTION OF THE INVENTION

The present invention is based upon the discovery that pellets of a sterically hindered phenol antioxidant exhibiting a balanced hardness such that the pellets avoid the problem of dust and abrasion while being readily dispersible in a host plastic can be produced when using as an initial binder for the sterically hindered phenol antioxidant a solution formed by dissolving a first portion of the antioxidant to be pelleted into a solvent for the antioxidant. The resulting paste is then extruded and the resulting extrudate cut so as to form pellets which are then dried.

While any solvent which is capable of dissolving the particular sterically hindered phenol antioxidant which is desired to be pelleted can be employed in the practice of this invention a presently preferred solvent is one selected from the group consisting of methylchloride, chloroform, toluene, acetone, methyl ethyl ketone, xylene, cyclohexane, styrene, methylcyclohexane and hexane. The presently preferred solvents are acetone and methylethylketone.

The antioxidant of the sterically hindered phenol type are well known for organic materials and are frequently used for the stabilization of polymers. Such compounds preferably contain at least one group of the formula:

in which R' is hydrogen, methyl or tert-butyl and R" is unsubstituted or substituted alkyl or substituted alkylthioalkyl.

Suitable sterically hindered phenol type antioxidants useful in the practice of the present invention are those selected from the group consisting of alkylated monophenols, alkylthiomethylphenols, hydroquinones, alkylated hydroquinones, tocophenols, hydroxylated thiodiphenyl ethers, alkylidene bisphenols, o, s, and s-benzyl compounds, hydroxybenzylated malonates, hydroxybenzyl aromatics, triazines, benzylphosphonates, acylaminophenols, esters of β-(5 tert-butyl-4-hydroxy-3-methylphenyl) propionic acid, esters of β-(3,5-dicyclo-hexyl-4-hydroxyphenyl)propionic acid, esters of 3,5-di-tert-butyl-4-hydroxyphenylacetic acid, and amides of β-(3,5-di-tert-butyl-4-hydroxyphenyl) propionic acid.

Presently preferred sterically hindered phenol antioxidants for the practice of the present invention is one selected from the group consisting of:

Octadecyl 3,5-di-t-butyl-4-hydroxyhydrocinnamate,

Tetrakis [methylene(3,5-di-t-butyl-4-hydroxylhydrocinnamate)]methane, 1,3,5-trimethyl-2,4,6-tris-(3,5-di-t-butyl-4-hydroxybenzyl)benzene, 1,3,5-Tris-(3,5-di-t-butyl-4-hydroxybenzyl) isocyanurate, 1,3,5-Tris-(4-t-butyl-3-hydroxy-2,6-dimethylbenzyl)-1,3,5-triazine- 2,4,6-(1H, 3H, 5H) trione, Thiodiethylbenebis-(3,5-di-t-butyl-4-hydroxy) hydrocinnamate, and 1,3,5-trimethyl-2,4,6-tris-(3,5-di-t-butyl-4-hydroxybenzyl) benzene.

Presently the most preferred antioxidant for the practice of this invention is 1,3,5-trimethyl-2,4,6-tris-(3,5-di-tert-butyl-4-hydroxybenzyl) benzene. Such antioxidant is a product of Albemarle Corporation and available under the trademark ETHANOX® 330.

In carrying out the process of the present invention, the solvent system can also contain from 0 to about 80 weight percent of an alcohol of the formula ROH wherein R is an alkyl group of 1 to 8 carbon atoms. Through the addition of the alcohol to the solvent system utilized for the forming of a paste of the sterically hindered phenol antioxidant there is achieved a continuing modification of the hardness of the resulting pellets such that as the percent content of the alcohol in the system increases there is affected a decrease in the hardness value of the pellet thus permitting the custom formation of an antioxidant pellet having a predetermined hardness such that there is a balance between that hardness required for the avoiding of abrasion and thus dust and that hardness which will permit the ready dispersion of the pelleted antioxidant in the host plastic for same. Thus the effect of the alcohol in the system is inverse to the amount of alcohol present in the solvent/alcohol system.

Presently preferred alcohols for use in the practice of the present invention is one selected from the group consisting of methanol, ethanol and isopropanol. The alcohol of particular preference at this time is methanol.

As used herein the term "plastic" is intended to mean organic polymers such as the olefin polymers of ethylene and propylene or mixtures thereof with other olefin monomers.

As used herein the term "pellet" is intended to mean a small, rounded, or spherical body of a sterically hindered phenol antioxidant which has been produced through the pelleting of same as in a pellet mill. Such pellets are typically cylindrical with width dimension in the range of about 1 to about 10 mm, preferably about 1–5 mm and a length being from about 1 to about 5 times the dimension of the width. Such pellets then have an aspect ratio (l/w) in the range of about 1 to about 5. Such materials are readily formed by a wide variety of pelleting apparatus which are well known to those in the art and as such the particular pelleter employed is not critical to the practice of the present invention. One such suitable pelleter is the Kahl pelleting press available from LCI Corporation.

The term "antioxidant" is intended to mean a sterically hindered phenol type antioxidant compound which contains at least one group of the formula

in which R' is hydrogen, methyl or tert-butyl and R' is a substituted or unsubstituted alkyl or substituted alkylthioalkyl.

The term "solution" as used in the description of the present invention means the mixture formed by dissolving in the selected solvent at least 1 gram of antioxidant per 100 mL of solvent. Such a solution can additionally have from 0 to about 80 weight percent of an alcohol having the formula ROH wherein R is a alkyl group of 1 to 8 carbon atoms.

The term "balanced hardness" is intended to mean that hardness of a pellet of a sterically hindered phenol antioxidant which is required to permit the handling so as to avoid abrasion while at the same time permitting the pellet to be readily processed in conventional dispensing systems.

Through the practice of the present invention there is provided a process for the production of novel pellets comprising a sterically hindered phenol antioxidant which exhibit a controlled hardness and which avoid the introduction of extraneous materials into the additive formulation.

Through the addition of controlled amounts of the alcohol to the solvent system there is achieved a control of the friability or hardness of the ultimately produced pellet.

While in one presently preferred embodiment of this invention there is provided pelletized product of ETHANOX® 330 which has a balance of hardness so as to permit transportation while being readily dispersed in the compounding of same in organic polymers, it will be appreciated that other antioxidants can likewise be employed in the practice of this invention either alone or in combination with other selected ingredients or coadditives. Thus through the process of this invention there can be produced customized additive systems having a balance of hardness which employ the selected sterically hindered phenolic antioxidant either alone or in combination with other desired additives for introduction into the host organic polymer.

The amount of the antioxidant of the sterically hindered phenol type in the pellets of the present invention will depend on the intended use of the pelleted additive. Thus the pellets of this invention can consist of 100% by weight of sterically hindered phenol antioxidant. However when formed in admixture with other components of a desired additive system the pellets should contain at least about 20% by weight of the sterically hindered phenol antioxidant.

Besides the sterically hindered phenol antioxidant, the pellets of this invention can also contain a secondary phosphite antioxidant such as phosphites, phosphonates, and fluorophosphonates. The amount of such secondary phosphite antioxidant will depend on the intended use of the pelleted additive system. Thus the pellets can contain from 0 to about 80% by weight of such secondary phosphite antioxidants. Examples of suitable secondary phosphite antioxidants are:

2,2'-Ethylidenebis-(4,6-di-t-butylphenyl)-Fluorophosphonite, 2,2', 2"-nitro[triethyl-tris (3, 3, 5,5-tetra-t-butyl- 1, 1'-biphenyl-2,2'-diyl)] phosphite, Tris(2,4-di-t-butylphenyl) phosphite, Bis(2,4-di-t-butylphenyl)pentaerythritol-di-phosphite, and Tetrakis (2,4-di-t-butylphenyl)-4,4'-biphenylenediphosphonite.

The amount of secondary phosphite antioxidant used will depend on the intended use of the plastic additive package. Such pellets can contain from 0 to about 80 percent by weight, preferably from about 3 to 70 percent by weight of secondary phosphite antioxidant. When in addition to the sterically hindered phenol antioxidant there is employed a secondary phosphite antioxidant, the weight ratio between the sterically hindered phenol antioxidant and the secondary phosphonite antioxidant is within the range of from about 20:1 to about 1:20 and preferably from about 2:1 to about 1:4.

In addition, the pellets of the present invention can contain a compound from the series consisting of the hydrotalcites, metal carbonates and metal oxides. Such compounds are well known for achieving acid neutralization in an additive system. When so used in combination with the sterically hindered phenol antioxidant, such further component can be present in an amount in the range of from 0 to about 80 percent by weight.

Hydrotalcites are well known and commercially available form Kyowa Chemical Company of Japan.

Presently preferred metal oxides are the oxides of divalent metals. Such compounds includes the oxides of zinc and magnesium.

Presently preferred metal carbonates are the carbonates of divalent metals. Such compounds includes the carbonate of calcium.

Other compounds which can be included in the additive pellet system of this invention include those plastic additives selected from the group consisting of metal soaps, antistatics, antiblocking agents, flame proofing agents, thioesters, internal and external lubricants, pigments, UV absorbers and light stabilizers.

In carrying out the process of this invention, the initially selected solvent for the antioxidant can be used alone or can have added thereto from 0 to 80 weight percent of the selected lower alkyl alcohol. The initial dissolving of antioxidant into the selected solvent system can be carried out separately from the total antioxidant mass to be pelletized in accordance with the present invention or the solvent system can be added to the antioxidant powder in an amount such that at least I gram of antioxidant per 100 mL of solvent is dissolved in the solvent and the resulting solution is brought in situ into contact with the remaining antioxidant powder so as to effect the formation of a paste of the antioxidant which is suitable for extrusion in a pellet mill. Typically, the concentration of the solvent processing aid (i.e., selected solvent plus alcohol, if any) required to form the paste which is suitable for extrusion in a pellet mill ranges from about 3 parts by weight solvent processing aid per 97 parts by weight of additive powder (i.e., phenolic antioxidant plus optionally secondary phosphite antioxidant and acid neutralizer) to about 20 parts by weight of solvent processing aid per 80 parts by weight of additive powder.

EXAMPLES

The following examples are intended to be illustrative of the present invention and to teach one of ordinary skill how to make and use the invention. These examples are not intended to limit the invention in any way.

In the examples, proccessability testing or pellet hardness measurements to determine the proccessability characteristics of the pellets i.e. hardness and attrition resistance was determined by subject the pellets to manual manipulation so as to observe the friability of the pellet.

EXAMPLE I 4000 grams of 1,3,5-trimethyl-2,4,6-tris-(3,5-di-tert-butyl-4-hydroxy-benzyl) benzene (ETHANOX® 330 antioxidant obtained from Albemarle Corporation) and 444 grams of anhydrous acetone were combined in a Kahl Model KDHJ-20 batch kneader and then blended for about 3 minutes. The resulting pasty powder blend was then transferred to a polyethylene bag, the bag was sealed and the material was stored for about 15 minutes. The blend was then manually fed to a Kahl Model 14–175 pellet mill operating at 100 rpm and equipped with a die plate having 2 mm diameter holes and a 6 mm pressway length. The pelletized product was then dried in a 200° F. oven for about 2 hours to yield a product consisting of 94% pellets and 6% fines (−20 mesh particles). The resulting pellets were relatively very hard, in the sense that considerable force was required to break them down into powder when subjected to manual compression and therefore could be handled with typical conveying equipment with minimal attrition.

For comparative purposes neat ETHANOX® 330 antioxidant powder was processed on a pellet mill operating under the same conditions as above described but in which no acetone was introduced. The products from the pellet mill consisted of nearly all powder with a few very soft pellets. This comparative example illustrates that the processing liquid such as acetone of the instant invention is necessary to impart the desired hardness to the pellets.

EXAMPLE II

Fourteen batches of feed material were prepared as follows: 1.33 kg of ETHANOX® 330 antioxidant powder and 2.67 kg of Irgafos 168 powder (obtained from Ciba Specialty Products) were combined in a Kahl model KDIIJ-20 batch kneader then dry blended for 5 minutes. 571 g of acetone was added to the powder in the kneader and blending was then continued for an additional 3 minutes. The resulting pasty solid blend was discharged from the kneader into a polyethylene bag which was then sealed. The fourteen batches of feed material were then manually fed to a Kahl Model 33–390 pellet mill operating at 80 rpm speed and equipped with a die plate having 3 mm diameter holes and a pressway length of 9 mm. The product obtained from the pellet mill was dried in a 200° F. oven for about two hours. Dry sieving of the dried product with a US Standard mesh screen indicated that the product consisted of 95.8% pellets (+12 mesh) and 4.2% fines (−12 mesh). The dried pellets exhibited adequate hardness and thus judged suitable for handling with conventional conveying equipment without significant attrition.

EXAMPLE III

A pelletized blend composition consisting of ETHANOX® 330 antioxidant blended with Irgafos 168 secondary phosphite antioxidant, dihydrotalcite from Kyowa Chemical Company and glycerol was prepared as follows: 2.63 kg of ETHANOX® 330 antioxidant, 1.215 kg of Irgafos 168 and 0.790 kg of dihydrotalcite were combined in a Kahl Model KDHJ-20 batch kneader and dry blended for 5 minutes. 0.263 kg of glycerol and 0.556 kg of anhydrous acetone were added to the kneader and blending was continued for an additional 3 minutes. The pasty mass from the kneader was transferred to a polyethylene bag for about 15 minutes storage. The mass was then manually fed to a Kahl Model 14-175 pellet mill operating at 100 rpm and equipped with a die plate having 3 mm diameter holes and a pressway length of 9 mm. The product from the pellet mill was collected and dried at 200° F. for about 2 hours. The dried product consisted of 93.9% pellets and only 6.1% fines (i.e. −12 mesh particles). The dried pellets were subjected to manual characterization and judged to have very good hardness and therefore good resistance to particle attrition during pellet conveying operations.

EXAMPLE IV

The process of Example III was repeated with half of the acetone processing solvent replaced with isopropanol. The resulting pellets were determined to be not as hard as those obtained in Example III but the hardness through manual characterization was judged to be sufficient to impart sufficient attrition resistance in the pellet conveying operation while exhibiting sufficient softness to permit the ready dispersion of the antioxidant pellet in to a host polymer.

EXAMPLE V

The process of Example III was repeated with the 0.556 kg of anhydrous acetone replaced by 0.319 kg of methylethylketone. The dried pellets were subjected to manual characterization and judged to have very good hardness and therefore good resistance to particle attrition during pellet converging operations. This example also illustrates that methylethylketone may be employed at relatively low concentrations in the process of this invention and, therefore, is a preferred solvent in terms of the economics of carrying out the process.

The specific examples herein disclosed are to be considered as being primarily illustrative. Various changes beyond those described will occur to those skilled in the art and such changes are to be understood as forming a part of this invention as they fall within the spirit and scope of the appended claims.

That which is claimed is:

1. A process for the production of pellets of a sterically hindered phenol antioxidant having a balanced hardness which comprises
   (a) dissolving a first portion of said sterically hindered phenol antioxidant in a solvent consisting essentially of at least one solvent of the group consisting of methylene chloride, chloroform, toluene, acetone, methylethylketone, xylene, cyclohexane, styrene, methylcyclohexane and hexane so as to form a solution of said sterically hindered phenol antioxidant in said solvent;
   (b) contacting a second portion of said sterically hindered phenol antioxidant with said solution of step (a) in an amount sufficient to form a paste of said second portion of said sterically hindered phenol antioxidant;
   (c) extruding the resulting paste of said sterically hindered phenol antioxidant as formed in step (b) so as to form strands thereof;
   (d) cutting the resulting strands of said sterically hindered phenol antioxidant as formed in step (c) so as to form pellets thereof;
   (e) drying the resulting pellets of said sterically hindered phenol antioxidant as formed in step (d) so as to form dried pellets thereof having a balance hardness.

2. The process of claim 1 wherein said sterically hindered phenol is at least one compound selected from the group consisting of alkylated monophenols, alkylthiomethylphenols, hydroquinones, alkylated hydroquinones, tocophenols, hydroxylated thiodiphenyl ethers, alkylidene bisphenols, o, s, and s-benzyl compounds, hydroxybenzylated malonates, hydroxybenzyl aromatics, triazines, benzylphosphonates, acylamino-phenols, esters of β-(5 tert-butyl-4-hydroxy-3-methylphenyl) propionic acid, esters of β-(3,5-dicyclohexyl-4-hydroxyphenyl) propionic acid, esters of 3,5-di-tert-butyl-4-hydroxy-phenylacetic acid, and amides of β-(3,5-di-tert-butyl-4-hydroxyphenyl) propionic acid.

3. The process of claim 2 wherein said sterically hindered phenol antioxidant is a member of the group consisting of Octadecyl 3,5-di-t-butyl-4-hydroxyhydrocinnamate,
Tetrakis [methylene(3,5-di-t-butyl-4hydroxylhydrocinnamate)]methane,
1,3,5-trimethyl-2,4,6-tris-(3,5-di-t-butyl-4-hydroxybenzyl)benzene,
1,3,5-Tris-(3,5-di-t-butyl-4-hydroxybenzyl) isocyanurate,
1,3,5-Tris-(4-t-butyl-3-hydroxy-2,6-dimethylbenzyl)-1,3,5-triazine-2,4,6-(1H, 3H,5H) trione, Thiodiethylbenebis-(3,5-di-t-butyl-4-hydroxy) hydrocinnamate, and 1,3,5-trimethyl-2,4,6-tris-(3,5-di-t-butyl-4-hydroxybenzyl) benzene.

4. The process of claim 1 wherein said sterically hindered phenol antioxidant is 1,3,5-trimethyl-2,4,6-tris (3,5-di-tert-butyl-4-hydroxybenzyl) benzene.

5. The process of claim 4 wherein said solvent is acetone.

6. The process of claim 1 wherein said solvent is methylethylketone.

7. The process of claim 1 wherein said solution contains at least 1 gram of said sterically hindered phenol antioxidant per 100 ml of solvent.

8. The process of claim 7 wherein the amount of said solution in step (b) is in the range of about 3 parts by weight per 97 parts by weight of said sterically hindered phenol antioxidant to about 20 parts by weight per 80 parts by weight of said sterically hindered phenol.

9. The process of claim wherein said dried pellets have a diameter of about 1 to about 10 mm and have an aspect ratio in the range of about 1 to about 5.

10. A process for the production of pellets of a sterically hindered phenol antioxidant having a balanced hardness which comprises dissolving a first portion of said sterically hindered phenol antioxidant in a solvent system consisting of at least one solvent of the group consisting of methylene chloride, chloroform, toluene, acetone, methylethylketone, xylene cyclohexane, styrene, methylcyclohexane, and hexane and from 0 to about 80 weight percent of an alcohol of the formula ROH wherein R is an alkyl group of from 1 to 8 carbon atoms, said alcohol being in amounts to said solvent such that as the amount of said alcohol added is increased, there is achieved a decrease in the balanced hardness of the pellet of said sterically hindered phenol antioxidant formed therewith and as the amount of said alcohol is decreased, there is achieved an increase in the balanced hardness of the pellet of said sterically hindered phenol antioxidant formed therewith;

(b) contacting a second portion of said sterically hindered phenol antioxidant with the solution of solvent and alcohol and sterically hindered phenol antioxidant dissolved therein in an amount sufficient to form a paste of said second portion of said sterically hindered phenol antioxidant;

(c) extruding the resulting paste of said sterically hindered phenol antioxidant so as to form strands thereof;

(d) cutting the resulting strands of said sterically hindered phenol so as to form pellets thereof; and (e) drying the resulting pellets of said sterically hindered phenol antioxidant so as to form dried pellets thereof having a balanced hardness which is inverse to the amount of alcohol present in the solvent/alcohol system.

11. The process of claim 10 wherein said sterically hindered phenol is at least one compound selected from the group consisting of alkylated monophenols, alkylthiomethyl-phenols, hydroquinones, alkylated hydroquinones, tocophenols, hydroxylated thiodiphenyl ethers, alkylidene bisphenols, o, s, and s-benzyl compounds, hydroxybenzylated malonates, hydroxybenzyl aromatics, triazines, benzylphosphonates, acylaminophenols, esters of β-(5 tert-butyl-4-hydroxy-3-methylphenyl) propionic acid, esters of β-(3,5-dicyclohexyl-4-hydroxyphenyl) propionic acid, esters of 3,5-di-tert-butyl-4-hydroxyphenylacetic acid, and amides of β-(3,5-di-tert-butyl-4-hydroxyphenyl) propionic acid.

12. The process of claim 11 wherein said sterically hindered phenol antioxidant is a member of the group consisting of Octadecyl 3,5-di-t-butyl-4-hydroxyhydrocinnamate, Tetrakis [methylene(3,5-di-t-butyl-4-hydroxylhydrocinnamate)]methane, 1,3,5-trimethyl-2,4,6-tris-(3,5-di-t-butyl-4-hydroxybenzyl)benzene, 1,3,5-Tris-(3,5-di-t-butyl-4-hydroxybenzyl) isocyanurate, 1,3,5-Tris-(4-t-butyl-3-hydroxy-2,6-dimethylbenzyl)-1,3,5-triazine-2,4,6-(1H, 3H, 5H) trione, Thiodiethylbenebis-(3,5-di-t-butyl-4-hydroxy) hydrocinnamate, and 1,3,5-trimethyl-2,4,6-tris-(3,5-di-t-butyl-4-hydroxybenzyl) benzene.

13. The process of claim 11 wherein said sterically hindered phenol antioxidant is 1,3,5-trimethyl-2,4,6-tris(3,5-di- tert-butyl-4-hydroxybenzyl) benzene.

14. The process of claim 10 wherein said alcohol is selected from the group consisting of methanol, ethanol, and isopropanol.

15. The process of claim 13 wherein said solvent is acetone and said alcohol is methanol.

16. The process of claim 13 wherein said solvent is methylethylketone and said alcohol is methanol.

17. The process of claim 1 wherein there is additionally present with said sterically hindered phenol a secondary phosphite antioxidant.

18. The process of claim 17 where the ratio of said sterically hindered phenol to said secondary phosphite antioxidant is in the range of about 1:20 to about 20:1.

19. The process of claim 10 wherein there is additionally present with said sterically hindered phenol a secondary phosphite antioxidant.

20. The process of claim 19 wherein the ratio of said sterically hindered phenol to said secondary phosphite antioxidant is in the range of about 1:20 to about 20:1.

21. The process of claim 17 wherein there is additionally present an acid neutralizer.

22. The process of claim 21 wherein said acid neutralizer is selected from the group consisting of a metal oxide, metal carbonate, and a hydrotalcite.

23. The process of claim 21 wherein said acid neutralizer is a hydrotalcite.

24. The pelleted sterically hindered phenol antioxidant product of the process of claim 1.

25. The pelleted sterically hindered phenol antioxidant product of the process of claim 4.

26. The pelleted sterically hindered phenol antioxidant product of the process of claim 10.

27. The pelleted sterically hindered phenol antioxidant product of the process of claim 19.

28. The pelleted sterically hindered phenol antioxidant product of the process of claim 21.

* * * * *

UNITED STATES PATENT AND TRADEMARK OFFICE
CERTIFICATE OF CORRECTION

PATENT NO. : 6,056,898
DATED : May 2, 2000
INVENTOR(S) : John Semen

It is certified that error appears in the above-identified patent and that said Letters Patent is hereby corrected as shown below:

<u>Column 9,</u>
Line 19, reads, "9. The process of claim wherein .", and should read, -- 9. The process of claim 1 wherein . -- .

<u>Column 10,</u>
Line 47, reads, " consisting of a metal oxide, metal carbonate, and .", and should read, -- . consisting of a metal oxide, a metal carbonate, and . -- .

Signed and Sealed this

Twenty-first Day of August, 2001

Attest:

*Nicholas P. Godici*

NICHOLAS P. GODICI
*Attesting Officer*     *Acting Director of the United States Patent and Trademark Office*